United States Patent [19]

Hylton et al.

[11] 4,324,904
[45] Apr. 13, 1982

[54] PROCESSES FOR THE PREPARATION OF HYDRATROPIC ACIDS AND ESTERS

[75] Inventors: Thomas A. Hylton, Kalamazoo Township, Kalamazoo County; Jerry A. Walker, Oshtemo Township, Kalamazoo County, both of Mich.

[73] Assignee: The Upjohn Company, Kalamazoo, Mich.

[21] Appl. No.: 105,166

[22] Filed: Dec. 19, 1979

[51] Int. Cl.³ .............................................. C07C 69/76
[52] U.S. Cl. ..................................... 560/102; 560/20; 560/21; 560/23; 560/47; 560/59; 560/81; 560/82; 560/83; 560/85; 560/86; 562/435; 562/469; 562/479; 562/483; 562/488; 562/492; 260/340.2; 260/343; 260/465 D
[58] Field of Search ..................... 560/102, 59, 81, 82, 560/83, 86, 76, 21; 562/479, 492, 435, 483, 488, 469; 260/465 D

[56] References Cited

U.S. PATENT DOCUMENTS

| | | | |
|---|---|---|---|
| 3,240,824 | 3/1966 | Boudakian et al. | 568/937 |
| 3,624,142 | 11/1971 | Shen et al. | 562/492 |
| 3,755,427 | 8/1973 | Adams et al. | 204/224 M |
| 3,784,705 | 1/1974 | Adams et al. | 424/317 |
| 3,793,457 | 2/1974 | Adams et al. | 424/287 |
| 3,901,906 | 8/1975 | Kozlik | 560/102 |
| 3,959,364 | 5/1976 | Armitage et al. | 562/492 |
| 3,992,459 | 11/1976 | Utne et al. | 560/59 |

FOREIGN PATENT DOCUMENTS 1316312 5/1973 United Kingdom.
1469700 4/1977 United Kingdom.
1514082 6/1978 United Kingdom.

OTHER PUBLICATIONS

Carney, et al., "A Potent Non-Steroidal Anti-Inflammatory Agent: 2-[3-chloro-4-(3-pyrrolinyl)phenyl]propionic acid," Experientia 29/8, p. 938, (Aug. 15, 1973).
Makosza et al., "Reactions of Organic Anions, Part LVIII. The Problem of Competitive Nucleophilic Substitution of Ortho- and Para-Halogens in 2,4-Dihalo Nitrobenzenes by some Carbanions", Roczniki Chemii Ann. Soc. Chim. Polonorum 50, p. 1850 (1976).
March in Advanced Organic Chemistry: Reactions, Mechanisms, and Structure, pp. 550–551, 1968 (McGraw-Hill, Inc.).
Cadogan in J. Chem. Soc., p. 4257 (1962).
J. Med. Chem. 10, 1078 (1967).
Tetrahedron Letters 215 (1967), 957 (1973).

Primary Examiner—Paul J. Killos
Attorney, Agent, or Firm—Joan Thierstein

[57] ABSTRACT

The invention concerns the novel compounds dialkyl 2-(3-fluoro-4-nitrophenyl)-2-methylmalonate IIIa and dialkyl 2-(3-fluoro-4-aminophenyl)-2-methylmalonate IVa useful as intermediates in an improved process for making 2-(2-fluoro-4-biphenylyl)propionic acid, known as flurbiprofen, having the formula

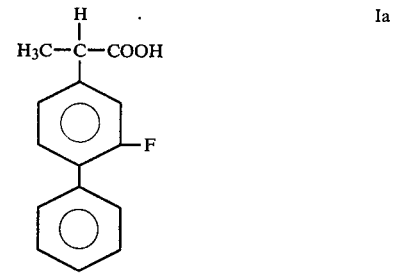

and ester thereof. It has anti-inflammatory activity which is about 240 times that of aspirin and analgesic activity which is about 180 times that of aspirin in standard laboratory tests. However, despite this high activity, the toxicity ($LD_{50}$) is only 1.2 to 2.4 times greater than that of aspirin in standard laboratory tests.

Also within the invention is a novel method of making the above intermediates and analogs thereof useful to prepare corresponding biaryl compounds which have pharmaceutical uses.

56 Claims, No Drawings

PROCESSES FOR THE PREPARATION OF HYDRATROPIC ACIDS AND ESTERS

FIELD OF THE INVENTION

The invention concerns the novel compounds dialkyl 2-(3-fluoro-4-nitrophenyl)-2-methylmalonate IIIa and dialkyl 2-(3-fluoro-4-aminophenyl)-2-methylmalonate IVa useful as intermediates in an improved process for making 2-(2-fluoro-4-biphenylyl)propionic acid, known as flurbiprofen, having the formula

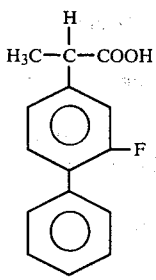

Ib and esters thereof. It has anti-inflammatory activity which is about 240 times that of aspirin and analgesic activity which is about 180 times that of aspirin in standard laboratory tests. However, despite this high activity, the toxicity ($LD_{50}$) is only 1.2 to 2.4 times greater than that of aspirin in standard laboratory tests.

Also within the invention is a novel method of making the above intermediates and analogs thereof useful to prepare corresponding biaryl compounds which have pharmaceutical uses.

DESCRIPTION OF THE PRIOR ART

Diethyl 2-(3-chloro-4-nitrophenyl)-2-methylmalonate and diethyl 2-(3-chloro-4-aminophenyl)-2-methylmalonate are known as intermediates for the preparation of tertiary amino acid derivatives of 2-(3-chloro-4-aminophenyl)-2-propionic acid having anti-inflammatory properties. For example, see Carney, et al, "A Potent Non-Steroidal Anti-Inflammatory Agent: 2-[3-chloro-4-(3-pyrrolinyl)phenyl]propionic acid," Experientia 29/8, p 938 Aug. 15, 1973); and British Pat. No. 1,316,312 partially corresponding to Swiss Pat. Nos. 574,921-2, 574,924-6. Particularly note Example 1 of Swiss Pat. No. 574,924 and further Makosza, et al, "Reactions of Organic Anions, Part LVIII. The Problem of Competitive Nucleophilic Substitution of Ortho- and Para-Halogens in 2,4-Dihalo Nitrobenzenes by some Carbanions", Roczniki Chemii Ann. Soc. Chim. Polonorum 50, p. 1850 (1976).

U.S. Pat. No. 3,755,427 and U.S. Pat. No. 3,793,457 discloses a 9-step synthesis of flurbiprofen starting from 4-bromoacetophenone. Other processes are disclosed in U.S. Pat. Nos. 3,784,705; 3,901,906; 3,959,364; 3,624,142; Belgium No. 840,354; German No. 2,533,397; Japan Kokai No. 75, 40,540 (1975); and German No. 2,613,812, as well as others. In these published methods, a number of intermediates are involved and/or potentially hazardous reactions or intermediates are employed (i.e., the Schiemann reaction for the introduction of fluorine).

None of the above cited prior art references discloses the novel compounds IIIa and IVa recited herein. Further, contrary to the present invention, the references name no final species requiring the presently named novel compounds IIIa and IVa as intermediates in processes to make such species and, therefore, do not teach the compounds. In addition, reaction conditions recited in the references using sodium hydride as a base for similar displacement of chloride by malonates do not teach the methods of preparation in the present invention for either the above intermediates or analogs thereof. For example, although Makosza et al teaches the use of aqueous sodium and potassium hydroxide in such chloride displacement by 2-phenylalkanenitriles and phenylacetonitriles, it is noted that there is no suggestion to extend the use of these bases to the similar chloride displacement by malonate also discussed by Makosza et al. In fact, aqueous sodium hydroxide and potassium carbonate would be expected to interfere with the malonate-chloride displacement reaction by hydrolyzing the malonate. However, it is now found that unexpectedly good results are obtained by the present novel process for displacements by malonate using essentially nonaqueous alkali hydroxide or potassium carbonate in addition to providing the advantage of more easily handled bases for contemplated commercial use of the process.

Finally, the novel use of the intermediates IIIa and IVa and analogs thereof as now found to be unexpectedly advantageous in making biaryls for known pharmaceutical uses is not appreciated in the prior art, particularly in making flurbiprofen as described herein.

The methods of preparing biaryls herein are coupling processes which improve the known Gomberg or Gomberg-Bachmann reaction discussed by March in Advanced Organic Chemistry: Reactions, Mechanisms, and Structure, pages 550-551, 1968 (McGraw-Hill, Inc.). However, March noted that "yields are not high (usually under 40%) because of the many side reactions undergone by diazonium salts" which are described as intermediates therein. Cadogan in J. Chem. Soc., page 4257 (1962) discloses the use of pentyl nitrite as the diazotising agent with increasing yields of the named biaryls. Other more recent references, such as Neth. Appl. No. 6,500,865, 7/26/75; C.A. 64, 5005e (1966), and U.S. Pat. No. 3,992,459 disclose various coupling reactions, based on the Gomberg or Gomberg-Bachmann citations; however, none suggest the improvements of the present invention processes in which yields of biaryl compounds are unexpectedly increased.

SUMMARY OF THE INVENTION

A compound having the formula

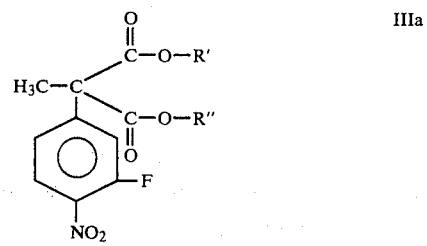

IIIa wherein R' and R" are the same or different and are selected from the group consisting of alkyl of from 1 to 6 carbon atoms, inclusive, or together form a cyclic diester.

A compound having the formula

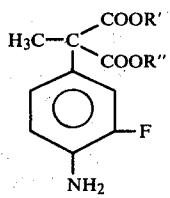   IVa wherein R' and R" are as defined above.

A process for the preparation of a compound selected from the group consisting of

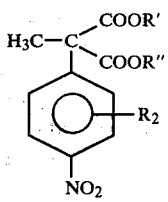   III wherein $R_2$ is selected from the group consisting of hydrogen, halogen, alkoxy of from 1 to 6 carbon atoms, inclusive, alkoxy carbonyl of from 1 to 6 carbons, inclusive, alkyl of from 1 to 6 carbons, inclusive, cycloalkyl of from 4 to 7 carbons, inclusive, phenyl, cyano, and nitro; which comprises reacting a compound having the formula

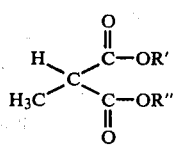

wherein R' and R" are as defined above with a compound selected from the group consisting of

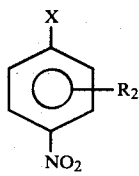   II wherein $R_2$ is as defined above and X is halogen; in the presence of a base selected from the group consisting of alkali metal hydroxide or potassium carbonate in an aprotic polar solvent such that the reaction mixture is essentially free of water.

Further, the present invention includes the above process in combination with an additional step in which the nitro group on compound III is reduced as illustrated by the following schematic:

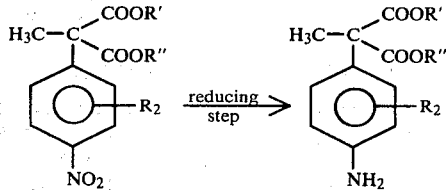

III   IV

Preferred compounds III and IV therein are those in which the $R_2$ group is a fluorine in the position ortho to the $NO_2$ group noted above as the novel compounds IIIa and IVa.

Another novel process includes the preparation of an intermediate having the formula

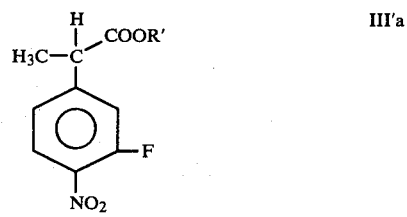   III'a wherein R' is as defined above which comprises reacting a compound having the formula

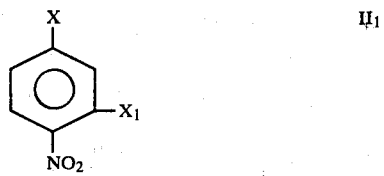   II$_1$ wherein X and $X_1$ may be the same or different and are halogen with the proviso that $X_1$ is not fluorine with the compound having the formula

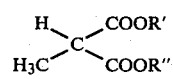

in the presence of a base to obtain a compound having the formula

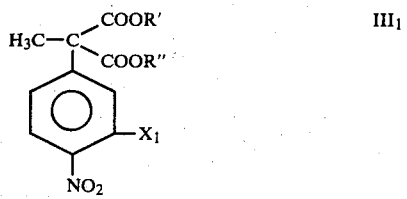   III$_1$ and (2) reacting the compound III$_1$ obtained in step (1) with an alkali metal fluoride to obtain compound III'a above.

Of course, this process can also be supplemented by the additional step in which the nitro group on compound III'a is reduced to prepare the preferred compounds IV'a having the formula

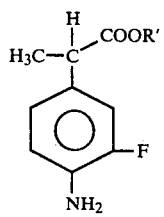 IV'a

The above processes require the selective displacement of X. When X is the same as $X_1$ displacement at X occurs preferentially because X is in a position para to the nitro substituent. However, when X is different than $X_1$ then in general, the ease of displacement of one halogen in the presence of another makes it necessary to limit X to a halogen more easily displaced than $X_1$. Thus, the ease of displacement for X with respect to $X_1$ in ranked order of least difficult to displace to most difficult to displace is shown by the following schematic:

$F >> Cl > Br > I$

Similarly, X is limited by the same dependency on its quality of displacement with respect to $R_2$ when $R_2$ is a halogen in the above processes.

Finally, the present invention is a total process for the preparation of a compound selected from the group consisting of

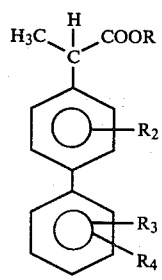 I wherein $R_2$ is defined as above and $R_3$ and $R_4$ are the same or different and are selected from the group consisting of hydrogen, hydroxyl, halogen, nitro, alkyl of from 1 to 6 carbons, inclusive, alkoxy of from 1 to 6 carbons, inclusive, alkoxycarbonyl having alkoxy of from 1 to 6 carbons, inclusive, aryloxycarbonyl, phenyl, cyano, and cyloalkyl of from 4 to 7 carbons, inclusive; and R is selected from the group consisting of hydrogen and alkyl of from 1 to 6 carbons, inclusive, which comprises (1) reacting a compound selected from the group consisting of

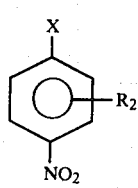 II with a compound having the formula

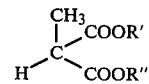

in the presence of a base to prepare a compound selected from the groups consisting of

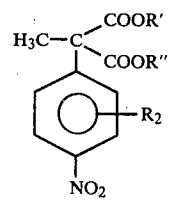 III wherein X, $R_2$, R' and R" are as defined above;

(2) reducing the nitro group of compound III from step 1 to produce a compound selected from the group consisting of

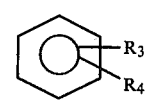 IV (3) coupling the compound IV of step 2 with a compound having the formula

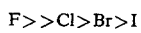 V to produce a compound selected from the group consisting of

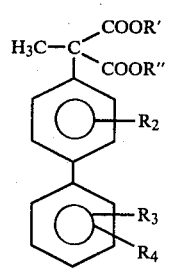 VI and (4) treating the product VI of step 3 to obtain the compound selected from the group consisting of I above.

In this total 4 step process, step 4 consists of decarboxylating and hydrolyzing to obtain either the ester Ia or acid Ib of compound I.

Alternative methods to make either the ester Ia or the acid Ib of compound I which differ from the above 4 step process by variations in the combination of steps disclosed above are also understood to be within the present invention and, for example, may be shown schematically as follows:

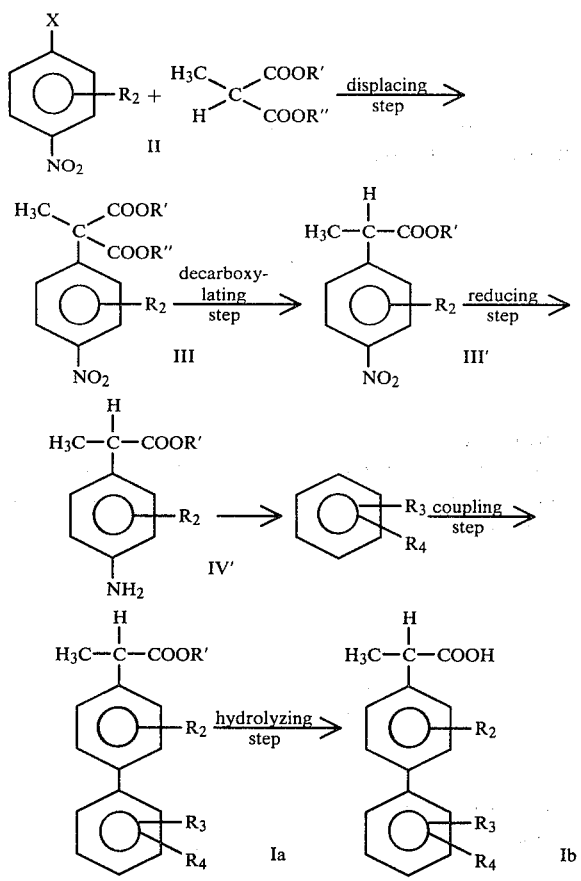

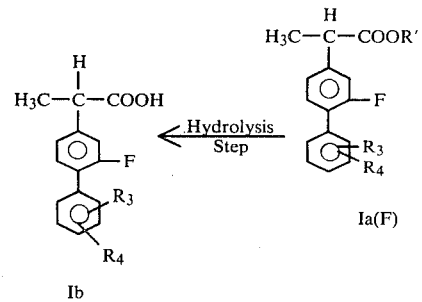

Preferred compounds I, i.e. both Ia and Ib, are those in which R₂ is fluorine on the position adjacent the biaryl linkage and R₃ and R₄ are both hydrogen.

Another variation in the combination of steps disclosed above which is to be understood to be within the present invention, including preferred compounds Ia or Ib, may also be shown by the following schematic:

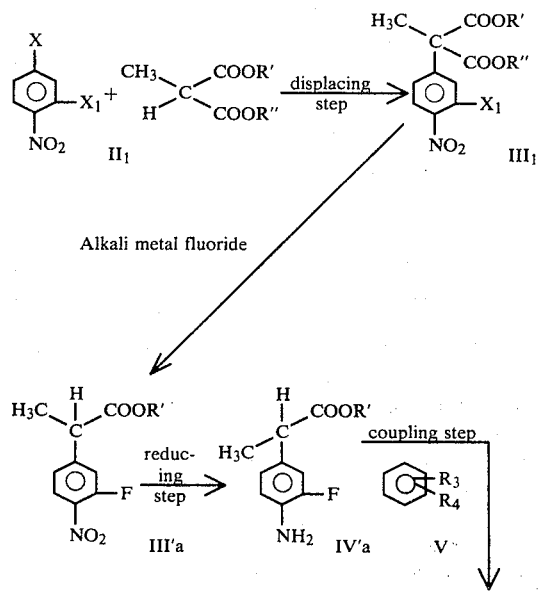

The term "base" above includes the teachings of the prior art to sodium hydride or the teachings of the present invention to sodium or potassium hydroxide and potassium carbonate.

The term "halogen" used herein denotes fluoro, chloro, bromo and iodo radicals.

Suitable alkyl radicals of from 1 to 6 carbons include, for example, methyl, ethyl, n-propyl, isopropyl, n-butyl, isobutyl, secondary butyl, tertiary butyl, n-pentyl, isopentyl, neopentyl, n-hexyl, and isomers thereof and together form a cyclic diester, similar to 2,2-dialkyl-1,3-dioxane-4,6-dione.

An alkoxy is one of the above mentioned alkyl radicals attached to an oxygen to form corresponding oxy radicals such as methoxy, ethoxy, etc.

Suitable cycloalkyls include, for example, cyclobutyl, cyclopentyl, cyclohexyl and cycloheptyl radicals.

Aryls as used in the term "aryloxycarbonyl" is e.q. phenyl or phenyl substituted with, for example, one or more halogen atoms.

In the present invention process, the intermediates generated and the reactions used offer a low-hazard potential compared to previously described processes. Also, the reactions can be carried out without purification of the intermediates. Thus, the invention provides a particularly efficient and economic process.

DETAILED DESCRIPTION OF THE INVENTION

The reaction of a substituted or unsubstituted 4-halonitrobenzene II with a dialkyl ester of 2-methylmalonic acid is carried out in the presence of a base, preferably an essentially non-aqueous base, such as alkali hydroxide e.g., sodium or potassium hydroxide or potassium carbonates; and with solid sodium hydroxide especially preferred. The sodium hydroxide in solid form comprises pellets, flakes or powder. The reaction is carried out in aprotic polar solvents, such as dimethylformamide and dimethylsulfoxide at a temperature of 0° C. to 100° C. Temperatures of from 25° C. to 35° C. and reaction times of 2 to 5 hours are preferred when using sodium hydroxide as the base. More rigorous reaction conditions, i.e., long reaction times or elevated temperatures are required when using potassium carbonate as the base. The reactants give high yields of compounds III when used in equimolar quantities and in concentration of about 0.75–0.88 molar solutions, however, other concentrations can be used. Generally, a very slight excess of both base and diethyl methylmalonate is preferred. The use of strictly anhydrous conditions or a preformed enolate is unnecessary in the above displacement reaction. However, the use of solvents such as methylene chloride and toluene in phase transfer conditions, taught for similar displacements by 2-phenylalkanenitriles and phenylacetonitriles of the prior art, are not effective for reactions carried out in the presence of sodium or potassium hydroxide and potassium carbonate bases.

Isolation of the compound III is accomplished by dilution of the reaction mixture with water and extraction therefrom of the compound III with an organic solvent, e.g. ethyl acetate. Further, purification is unnecessary for the reduction step of the invention process to obtain the preferred fluoro substituted intermediate IIIb noted above.

The reduction of the nitro group in compound III is accomplished by known methods such as catalytically with hydrogen and a noble metal catalyst or chemically using any one of a variety of well-known reducing agents, such as iron or tin in an aqueous acidic medium, with sodium dithionite or with zinc in acetic acid.

The catalytic reduction with hydrogen may be carried out by standard methods, e.g., in a Parr apparatus with compound III in solution. A variety of solvents can be used, such as lower alkanols, aliphatic hydrocarbons having a boiling point over 35° C., chlorocarbons, ethylacetate and the like, or aromatic liquid hydrocarbons. A variety of standard noble metal hydrogenation catalysts can be used with palladium or platinum on carbon being preferred. Hydrogen pressures of from 1 to several atmospheres can be used. Filtration removes the catalyst and the resulting compound IV in solution may be used without further purification in the coupling step of the invention process.

Chemical reduction can also be carried out, for example, with powdered iron in a water-ethanol mixture in the presence of ammonium chloride. A high conversion is obtainable at temperatures of about 50°–80° C. Best results for obtaining compound IV are by catalytic hydrogenation. Since the compound IV amine is sensitive to air in both the above reductions, a nitrogen atmosphere is used.

Although the Gomberg-Bachmann reactions as recited in the above cited references may be used as the coupling reaction in the total process of this invention, use of improved coupling reactions as taught in a copending application Ser. No. 279,134 filed June 30, 1981 which is a continuation of Ser. No. 105,062 filed Dec. 19, 1979 now abandoned is desirable. They are generally described as follows.

First in the preferred embodiment of the coupling reaction, a benzene solution of compound IV is added simultaneously with an acid to a nonaqueous mixture of excess compound V and solid sodium or potassium nitrite. Alternatively in this coupling reaction a benzene solution of compound IV is added simultaneously with an acid to a mixture of excess compound V and an aqueous solution of sodium or potassium nitrite. The ratio of the amount of compounds IV to V ranges from 5:10 to 1:10. The acid may be a mineral acid such as sulfuric acid or an organic acid such as benzoic, chloroacetic, dichloroacetic, trichloroacetic, methanesulfonic or acetic acid. The temperature of the reaction mixture is maintained between 25° C. and the boiling temperature of the mixture. Molar amounts of acid and sodium or potassium nitrite to that of compound IV are each in the range of 1 to 4 times, preferably 2.5 times. In an especially preferred embodiment the compound IV and acetic acid are added dropwise to a mixture of the aqueous or nonaqueous metal nitrite in the compound V. Stirring from 2 to 18 hours after the addition is completed at the preferred temperatures of the reaction is advantageous. The product VI is isolated by cooling the reaction mixture washing, evaporating, distilling, or other conventional procedures. A particularly simple and preferred workup is evaporation, dissolution in 85% aqueous sulfuric acid and extraction of the product into hexane. Crude product VI is obtained and further purification may not be necessary for use of the product in making compounds I or Ia. On the other hand, nitro compounds may be by-products in this reaction, so it may be advantageous to reduce the reaction mixture by adding iron/hydrochloric acid, zinc/acetic acid mixtures or sodium dithionite, which converts these by-products to amines, such that these can be removed from the product simply by washing with acid. Conditions for the reduction of nitro compounds are similar to those outlined by S. R. Faudler et al., in "Organic Functional Group Preparation", Vol. 1, Academic Press, New York, 1968, p. 339.

If the coupling reaction is carried out in nonaqueous conditions with solid metal nitrite, it is also advantageous to add an absorbent for water, such as anhydrous magnesium sulfate, silica gel or Celite ®. Furthermore, the use of potassum nitrite rather than sodium nitrite in this reaction gives a higher yield and is therefore among the preferred conditions for the anhydrous coupling reaction.

In addition to the above named acids for use in this reaction it is found that in the two phase aqueous reaction mixture hydrofluoric and fluoboric are effective. However, fluoboric acid ($HBF_4$) gives a particularly high and unexpected yield. If sulfuric acid is used a 10% solution is preferred.

In preparing the especially preferred diethyl 2-(2-fluoro-4-biphenylyl)-2-methyl malonate compound VI for use in subsequent reactions according to the novel methods described herein the temperature of the coupling reaction is 25° to 80° C. and preferably 68°–70° C.

The alternative coupling reaction, also noted above, employs alkyl nitrites instead of sodium nitrite and is accomplished in the absence of water. In this reaction a solution of the compound IV in excess benzene is reacted with alkyl nitrite such as isoamyl nitrite in the presence of the compound V at 20° to 80° C. over a period of 5 to 20 hours. Preferably in this embodiment of the invention, isoamyl nitrite and a solution of the compound IV in benzene are each added dropwise separately but simultaneously over a period of about 20 hours to an excess amount of the compound V while maintaining the temperature in the range of 25° C. to the boiling point of the solvent, preferably about 65° C. The product VI may be treated with a reducing agent and isolated in a manner analogous to that described above for the preferred coupling reaction using metal nitrite.

It is also understood that the above coupling reaction is not limited to the novel process conditions of the copending application described herein. For example, conditions similar to those described in U.S. Pat. No. 3,992,459 may be used to react compounds V and IV above. These conditions include the use of copper or copper salt.

Of particular interest is Example 5 wherein diethyl 2-(4-amino-3-fluorophenyl)-2-methyl malonate is substituted for the corresponding reactant, 2,4-difluoroaniline. However, some disadvantages exist in the recovery of the copper and/or disposal thereof which may distinguish the coupling reaction preparing VI of this invention noted above from U.S. Pat. No. 3,992,459. On the other hand, each of the noted coupling reactions disclosed herein may be further modified by conducting the reaction in the presence of copper. Especially preferred is the use of the nonaqueous medium with solid sodium or potassium nitrite described herein with copper. This copper may be in the form of a copper powder or a copper salt. However, if a copper powder is chosen reaction conditions are used which assure a timely preparation of copper salt in situ.

The step 4 treatment of compound VI which converts it to the acid Ib can be carried out by any known decarboxylation and hydrolysis. For example, compound VI may be reacted with an alkali hydroxide to obtain a dialkali salt thereof, acidified to obtain a malonic acid, and heated to achieve decarboxylation resulting in the desired acid Ib.

The first part of this process is preferably carried out in a nitrogen atmosphere with an alkali hydroxide in aqueous alkanol at 0°–25° C. The alkali hydroxide can be lithium, sodium, or potassium with sodium preferred. Alkanols such as methanol, ethanol, 1-propanol, 2-propanol can be used with aqueous ethanol preferred. The ratio of the alkai hydroxide to the diester VI is between 2.5 and 6 moles per mole of diester. After the saponification is complete, the reaction mixture is diluted and acidified with a mineral acid such as hydrochloric acid, dilute sulfuric acid, or an organic acid such as acetic acid. The thus produced free malonic acid is extracted with an organic solvent, e.g., ethyl acetate, methylene dichloride, and the like.

The extracted material is evaporated and the residue dissolved in glacial acetic acid and heated to reflux for 1 to 10 hours to effect decarboxylation. The resulting product is compound Ib, which is isolated and purified by conventional methods, e.g., evaporation, extraction, crystallization and the like.

The hydrolysis of the ester and decarboxylation of the diacid can also be carried out simultaneously by refluxing the malonate VI with acetic acid and a strong mineral acid. A good mixture for this is about 2-3 volume parts of acetic acid with 1 part of 4 N–8 N aqueous hydrochloric acid. The reaction time for the refluxing process is about 18–48 hours, for which reason the earlier base hydrolysis is preferred.

On the other hand treatment of the compound VI which converts it to the ester Ia or acid Ib can also be carried out by methods known to convert malonates directly to the desired monoesters, Ia or further hydrolyzing Ia if desired to Ib. A description of a similar conversion reaction may be found in J. Med. Chem. 10, 1078 (1967); Tetrahedron Letters 215 (1967) or Tetrahedron Letters 957 (1973). The highest yields and most amenable conditions preferred for use here are found in the latter of the above references in which compound VI is heated to temperatures of from 50° C. to 200° C. preferably 140° C. to 180° C. in a salt-solvent system of sodium chloride in wet dimethyl sulfoxide. Carbon dioxide and alkanols are produced in the reaction. Approximately 2 moles of water per mole of compound VI are added to the dimethyl sulfoxide to make it wet and a slight excess of sodium chloride is used.

Isolation of the desired compound Ia or Ib above is by conventional methods chosen for advantages dependent on the properties of the product.

In the alternative method of the total process of the present invention wherein the decarboxylation step follows the displacement step as shown by the schematic above, procedures similar to those taught by the cited references or generally described herein are used.

The reaction step disclosed above and as shown by the following schematic

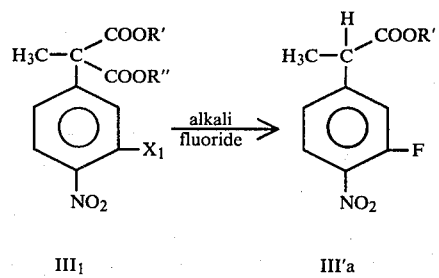

III$_1$      III'a may generally be accomplished by procedures similar to those described in U.S. Pat. No. 3,240,824, British Pat. Nos. 1,469,700 and 1,514,082. Decarboxylation occurs in this process.

It is understood that in the total 4 step process disclosed herein for the preparation of the biaryl substituted 2-propionic ester Ia or acid Ib, the individual steps may be accomplished by generally known reaction conditions. However, by utilizing the novel steps noted for various steps in combinations as set forth by the basic 4 step process optimum advantages accrue to the disclosure of these combinations.

For example, sodium hydride in a polar solvent under reaction conditions of prior art reference may be used to accomplish the displacing step for disclosed compounds also found herein. However, these reactants and the conditions required by their use cause the displacement reaction to be less economical, more hazardous and more inconvenient than the conditions now found to be useful in the present invention. Furthermore, the Gomberg and Gomberg-Bachman reactions described in the literature may be used in the coupling step but the novel improvements recited herein and now claimed in the noted co-pending application make this step less hazardous and more economical herein.

The following examples illustrate the process of this invention but are not to be construed as limiting.

Starting materials for preparing dialkyl 2-(3-fluoro-4-nitrophenyl)-2-methylmalonate and dialkyl 2-(3-fluoro-4-aminophenyl)-2-methylmalonate and for use in the processes of this invention are available or can be prepared by methods described in the prior art.

EXAMPLE 1

Diethyl 2-(3-fluoro-4-nitrophenyl)-2-methylmalonate III

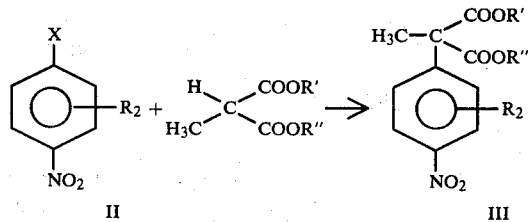

II      III

A mixture of 50.0 g (0.31 mol) of 2,4-difluoronitrobenzene II, 56.1 g (0.32 mol) of diethylmethylmalonate and 400 ml of dimethylformamide are vigorously stirred. To the stirring mixture is added 13.1 g (0.33 mol) sodium hydroxide in one portion at 25° C., cooling with ice to keep the temperature of the reaction mixture at 25°-30° C. during the first hour. Thereafter, stirring is maintained for 3.5 hours, then 800 ml of water is added, the organic layers removed, and the aqueous layer extracted with three 180-ml portions of ethyl acetate-water.

The cmbined organic layer and extracts are washed with diluted sodium sulfate (3 times; a total of 2 liters) and then with 100 ml of saturated sodium sulfate.

The solution is then dried over anhydrous sodium sulfate and concentrated in vacuo to give 114.0 g of diethyl 2-(3-fluoro-4-nitrophenyl)-2-methylmalonate III as an oil which is used as such in the next stop.

In like runs, the diethyl 2-(3-fluoro-4-nitrophenyl)-2-methylmalonate III is purified to give a light yellow oil of boiling range 149°-151° C. at about .02 mm Hg.

EXAMPLES 2 THROUGH 34

Other runs are carried out in a similar manner as Example 1 under the conditions stated in Tables I and II.

TABLE I

Condensation of DFNB with DEMM (with sodium hydroxide as base)

| Example | Solvent | Conc. DFNB M | Equiv. of Reaq. Used DFNB | DEMM | Base | Base Used | Rxn.[a] Temp. | Rxn. Time | % b Yield |
|---|---|---|---|---|---|---|---|---|---|
| 2 | DMF | 0.75 | 1.0 | 1.02 | 1.03 | Flaked NaOH | <30° | 5 hrs. | 79 |
|   | DMF | 0.75 | 1.0 | 1.02 | 1.03 | Flaked NaOH | <30° | 20 hrs. | 77 |
| 3 | DMF | 0.75 | 1.0 | 1.02 | 1.03 | Flaked NaOH | 24–30° | 6 hrs. | 88 |
| 4 | DMF | 0.75 | 1.0 | 1.02 | 1.03 | Flaked NaOH | 25° | 6 hrs. | 84 |
|   | DMF | 0.75 | 1.0 | 1.02 | 1.03 | Flaked NaOH | 25° | 20 hrs. | 79 |
| 5 | DMF | 0.75 | 1.0 | 1.02 | 1.03 | Powder NaOH | 25° | 6 hrs. | 84 |
|   | DMF | 0.75 | 1.0 | 1.02 | 1.03 | Powder NaOH | 25° | 20 hrs. | 75 |
| 6 | DMF | 0.75 | 1.0 | 1.02 | 1.03 | Flaked NaOH | 50° | 6 hrs. | 72 |
| 7 | DMF | 0.75 | 1.0 | 1.02 | 1.2 | Flaked NaOH | 25° | 3 hrs. | 87 |
| 8 | DMF | 0.75 | 1.0 | 1.02 | 1.2 | Flaked NaOH | <30° | 3 hrs. | 80 |
| 9 | DMF | 0.75 | 1.0 | 1.2 | 1.03 | Flaked NaOH | 25° | 6 hrs. | 81 |
| 10 | DMF | 0.75 | 1.0 | 1.13 | 1.2 | Flaked NaOH | 25° | 2 hrs. | 73 |
| 11 | DMF | 0.88 | 1.0 | 1.02 | 1.03 | Flaked NaOH | 25–30° | 6 hrs. | 87 |
| 12 | DMF | 0.88 | 1.0 | 1.02 | 1.2 | Flaked NaOH | <30° | 16 hrs. | 89 |
| 13 | DMF | 0.88 | 1.0 | 1.02 | 1.3 | Flaked NaOH | <30° | 16 hrs. | 74 |
| 14 | DMF | 0.88 | 1.0 | 1.02 | 1.2 | Flaked NaOH | 25° | 1 hr. | 74 |
|   | DMF | 0.88 | 1.0 | 1.02 | 1.2 | Flaked NaOH | 25° | 20 hrs. | 76 |
| 15 | DMF | 1.26 | 1.0 | 1.02 | 1.2 | Flaked NaOH | 25° | 1 hr. | 63 |
| 16 | DMF | 3.14 | 1.0 | 1.02 | 1.2 | Flaked NaOH | 25° | 1 hr. | 54 |
| 17 | DMF | 0.38 | 1.0 | 2.0 | 2.07 | Flaked NaOH | 25° | 20 hrs. | 60 |

[a] 25° = initial temperature = 25°, exotherm was not controlled; <30° = initial temperature 5-15° C., maintained below 30° C. throughout reaction; 25-30° C. = initial temperature 25°, temperature maintained between 25-30° C. throughout reaction.
DMF = dimethylformamide
DFNB = 2,4-difluoronitrobenzene
DEMM = diethyl 2-methylmalonate
b. Determined by gas liquid chromatography

TABLE II

Condensation of DFNB with DEMM (with carbonate as base)

| Example | Solvent | Conc. DFNB M | Equiv. of Reaq. Used DFNB | DEMM | Base | Base Used | Rxn. Temp. | Rxn. Time | % b Yield | Comments |
|---|---|---|---|---|---|---|---|---|---|---|
| 18. | DMF | 0.75 | 1.0 | 1.0 | 1.0 | A | 25° | 20 hrs. | | |
| 19. | DMF | 0.75 | 1.0 | 1.02 | 1.15 | A | 60° | 18 hrs. | 58 | |
| 20. | DMF | 0.75 |  | 1.02 | 1.1 | A | 60° | 19 hrs. | 65 | added (CH$_3$)$_4$NBF$_4$ |
| 21 | 10% aq. DMF | 0.75 | 1.0 | 1.02 | 1.1 | A | 60° | 18 hrs. | 37 | |
| 22. | DMF | 0.75 | 1.0 | 1.02 | 1.25 | A | 60° | ~23 hrs. | 60 | |
|   |   |   |   |   |   |   |   | ~50 hrs. | 81 | |
| 23. | DMF | 0.38 | 1.0 | 1.02 | 1.25 | B | 60° | 21 hrs. | 78 | |

TABLE II-continued
Condensation of DFNB with DEMM
(with carbonate as base)

| Example | Solvent | Conc. DFNB M | Equiv. of Reaq. Used DFNB | DEMM | Base | Base Used | Rxn. Temp. | Rxn. Time | % b Yield | Comments |
|---|---|---|---|---|---|---|---|---|---|---|
| 24. | DMF | 0.75 | 1.0 | 1.28 | 1.25 | A | 60° | 23 hrs. | 51 | |
|  |  |  |  |  |  | A |  | 53 hrs. | 73 | |
| 25. | DMF | 0.75 | 1.0 | 1.02 | 1.25 | B | 60° | 18 hrs. | 73 | |
|  |  |  |  |  |  | B | 60° | 43 hrs. | 75 | |
| 26. | DMF | 0.75 | 1.0 | 1.02 | 1.25 | A | 60° | 28 hrs. | 69 | pre-formed malonate |
| 27. | DMF | 0.75 | 1.0 | 1.02 | 1.5 | A | 60° | 25 hrs. | 58 | portionwise add'n. |
| 28. | DMF | 0.75 | 1.0 | 1.02 | 1.25 | A | 90° | 23 hrs. | 61 | |
| 29. | DMF | 0.75 | 1.0 | 1.02 | 1.25 | A | 120° | 20 hrs. | 77 | |
| 30. | DMF | 0.75 | 1.0 | 1.02 | 1.25 | B | 120° | 16 hrs. | 86 | |
| 31. | DMF | 0.75 | 1.0 | 1.02 | 1.25 | B | 140° | 2.5 hrs. | 73 | |
| 32. | DMF | 0.75 | 1.0 | 1.02 | 1.25 | B | 155° | 1 hr. | 79 | |
| 33. | DMF | 0.75 | 1.0 | 1.02 | 1.25 | $Na_2CO_3$ | 60° | 44 hrs. | 11 | |

A = anhydrous $K_2CO_3$(60 mesh)
B = anhydrous $K_2CO_3$(300 mesh)
DMF = dimethylformamide
DFNB = 2,4-difluoronitrobenzene
DEMM = diethyl 2-methylmalonate
b. Determined by gas liquid chromatography The examples confirm that yields above 85% can be obtained.

Though dimethylformamide is the preferred solvent, other aprotic polar solvents such as other amides, dimethylsulfoxide, sulfolane, hexamethyl phosphoric triamide, and others, can be used.

Using conditions similar to Examples 1-33, the following compounds III can be prepared:
dimethyl 2-(3-fluoro-4-nitrophenyl)-2-methylmalonate,
di-n-propyl 2-(3-fluoro-4-nitrophenyl)-2-methylmalonate,
diisopropyl 2-(3-fluoro-4-nitrophenyl)-2-methylmalonate,
di-n-butyl 2-(3-fluoro-4-nitrophenyl)-2-methylmalonate,
diisobutyl 2-(3-fluoro-4-nitrophenyl)-2-methylmalonate,
disecondarybutyl 2-(3-fluoro-4-nitro-phenyl)-2-methylmalonate,
ditertiarybutyl 2-(3-fluoro-4-nitro-phenyl)-2-methylmalonate,
di-n-pentyl 2-(3-fluoro-4-nitrophenyl)-2-methylmalonate,
diisopentyl 2-(3-fluoro-4-nitrophenyl)-2-methylmalonate,
dineopentyl 2-(3-fluoro-4-nitrophenyl)-2-methylmalonate,
di-n-hexyl 2-(3-fluoro-4-nitrophenyl)-2-methylmalonate,
diisohexyl 2-(3-fluoro-4-nitrophenyl)-2-methylmalonate,
dineohexyl 2-(3-fluoro-4-nitrophenyl)-2-methylmalonate,
methyl ethyl 2-(3-fluoro-4-nitrophenyl)-2-methylmalonate,
propyl butyl 2-(3-fluoro-4-nitrophenyl)-2-methylmalonate,
pentyl hexyl 2-(3-fluoro-4-nitrophenyl)-2-methylmalonate,

EXAMPLE 34

Alternate Method to Intermediate for Directly Making Monesters Ia

Ethyl-2-(3-fluoro-4-nitrophenyl)propionate

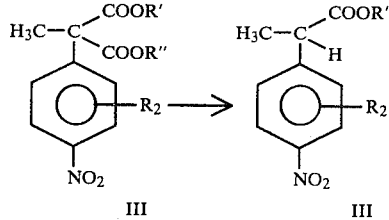

III → III

A mixture of 100 millimoles of diethyl 2-(3-fluoro-4-nitrophenyl)-2-methylmalonate, 110 millimoles of sodium chloride and 50 milliliters of dimethyl sulfoxide is heated under nitrogen at about 130° to 180° C. for about 6 hours. On cooling the mixture is diluted with 100 milliliters of water and 100 milliliters of ethyl acetate. The layers are separated and the organic layer is washed two times with 24 milliliters of water. After drying over disodium sulfate the organic layer is concentrated in vacuo to give the desired ethyl 2-(3-fluoro-4-nitrophenyl)propionate.

EXAMPLE 35

Diethyl 2-(4-amino-3-fluorophenyl)-2-methylmalonate IV

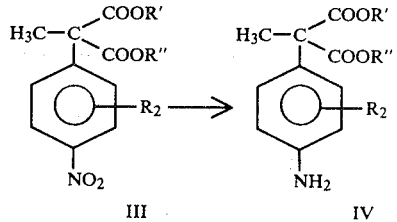

III → IV

To a solution of 41.6 g diethyl 2-(4-nitro-3-fluorophenyl)-2-methylmalonate III in 210 ml ethyl acetate in a 500-ml Parr hydrogenation bottle is added 830 mg (2 wt %) of 5% palladium/carbon. The mixture is hydrogenated in a Parr apparatus at 25° C. under 10–12 psi hydrogen for 2.5 hours. The catalyst is removed by filtration through diatomaceous earth (Celite ®) and is washed with a few ml of ethyl acetate. The solvent is removed in vacuo to give diethyl 2-(4-amino-3-fluorophenyl)-2-methylmalonate as a viscous oil, 37.6 g [100% wt. yield]. This material is used without purification.

Chemical Reduction of compound IIIa

To a solution of 9.86 g (31.51 mmol) diethyl 2-(4-nitro-3-fluorophenyl)-2-methylmalonate in 60 ml of 50% aqueous ethanol is added 10.0 g (186.92 mmol) of solid ammonium chloride followed by a 4.48 g (80.21 mmol, 2.55 equiv.) of 40 mesh activated iron filings.

The resulting mixture is stirred under nitrogen in an oil bath at 60° C. for 4.5 hours and let stand at room temperature for 12 hours. The reaction mixture is filtered through diatomaceous earth (Celite ®) and the solids are washed several times with 50% aqueous ethanol. The combined filtrates are concentrated in vacuo to remove most of the ethanol and are then diluted with 100 ml water. Extraction with 2×50 ml ethyl acetate gives an organic fraction which is washed with dilute aqueous sodium sulfate and dried over sodium sulfate. Concentration in vacuo gives 8.44 g (94.6% yield) diethyl 2-(4-amino-3-fluorophenyl)-2-methylmalonate (IVa) as a dark brown oil which gives by distillation an almost colorless oil of boiling point of about 190° C. at 0.1 mm Hg.

Since the amine in both reactions above is air sensitive (darkens on exposure), all manipulations can be carried out under nitrogen.

Similar to Example 35 the chemical reduction is repeated as shown in Examples 36 through 41 under the following conditions and with the following results (Table IV):

di-n-pentyl 2-(3-fluoro-4-aminophenyl)-2-methylmalonate,
diisopentyl 2-(3-fluoro-4-aminophenyl)-2-methylmalonate,
dineopentyl 2-(3-fluoro-4-aminophenyl)-2-methylmalonate,
di-n-hexyl 2-(3-fluoro-4-aminophenyl)-2-methylmalonate,
diisohexyl 2-(3-fluoro-4-aminophenyl)-2-methylmalonate,
dineohexyl 2-(3-fluoro-4-aminophenyl)-2-methylmalonate,
methyl ethyl 2-(3-fluoro-4-aminophenyl)-2-methylmalonate,
propyl butyl 2-(3-fluoro-4-aminophenyl)-2-methylmalonate,
pentyl hexyl 2-(3-fluoro-4-aminophenyl)-2-methylmalonate,
dimethyl 2-(3-fluoro-4-aminophenyl)-2-methylmalonate,

EXAMPLE 42

Diethyl 2-(2-fluoro-4-biphenylyl)-2-methylmalonate VI with the Nitrate and Acid Procedure

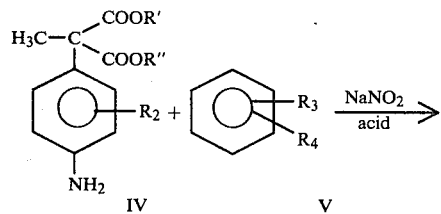

TABLE IV

| Example | Solvent | Acid | Iron Used[a] | Rxn. Time | Rxn. Temp. | Yield (%) |
|---|---|---|---|---|---|---|
| 36 | 50% EtOH aq. | 12N HCl | 40 mesh(activated) | 6 hrs. | 60° | ~80 |
| 37 | " | 20 mol. % / 12N HCl | " | 4 hrs. | 60° | ~80 |
| 38 | " | 10 mol. % / 12N HCl | powder(unactivated) | 4 hrs. | 60° | ~80 |
| 39 | 50% aq. EtOH | 6 eq. NH₄Cl | 40 mesh(activated) | 5 hrs. | 60° | ~95 |
| 40 | " | " | " | 20 hrs. | 25° | ~95 |
| 41 | " | " | powder(unactivated) | 5 hrs. | 60° | ~95 |

[a]Activation - 10 g 40 mesh iron filings is treated with 2 ml 12N aq. HCl, then dried under nitrogen. [See R.L. Jenkins, et al, Ind. Chem. Eng. 22, 31(1930)].

Using conditions similar to Example 34, the following compounds IV can be prepared:
dimethyl 2-(3-fluoro-4-aminophenyl)-2-methylmalonate,
di-n-propyl 2-(3-fluoro-4-aminophenyl)-2-methylmalonate,
diisopropyl 2-(3-fluoro-4-aminophenyl)-2-methylmalonate,
di-n-butyl 2-(3-fluoro-4-aminophenyl)-2-methylmalonate,
diisobutyl 2-(3-fluoro-4-aminophenyl)-2-methylmalonate,
disecondarybutyl 2-(3-fluoro-4-aminophenyl)-2-methylmalonate,
ditertiarybutyl 2-(3-fluoro-4-aminophenyl)-2-methylmalonate,

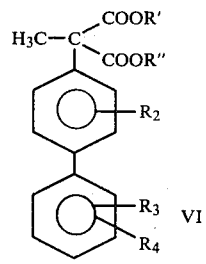

In a one-liter round bottom flask is placed 18.34 g (0.266 mol., 2 equiv.) of sodium nitrate, 22 ml of water, and 210 ml of benzene V. The mixture is placed in an oil bath at ~68°–70° C. and is stirred vigorously. A solution of 37.6 g of diethyl 2-(4-amino-3-fluorophenyl)-2-methylmalonate IV, 16.0 g (0.266 mol, 2 equiv.) of glacial acetic acid, and 70 ml of benzene are added from an addition funnel dropwise over ~6 hours. Heating is continued for 2 hours after addition is complete, and the mixture is then allowed to stand overnight. The resulting mixture is transferred to a one-liter separatory funnel and the benzene layer is washed with 3×100 ml of dilute aqueous sodium sulfate solution. Concentration in vacuo gives a dark brown viscous oil, 47.8 g.

The crude product VI is dissolved in 66.5 ml of aq. sulfuric acid (85% v/v) and the resulting solution is extracted with 4×500 ml hexane. The combined hexane extracts are washed with 4×500 ml 1 M aqueous sodium carbonate solution and 100 ml of saturated aqueous sodium sulfate. Removal of the solvent in vacuo gives 26.5 g of diethyl 2-(2-fluoro-4-biphenylyl)-2-methylmalonate VI as a light yellow viscous oil (58% yield overall from difluoronitrobenzene II).

In a manner similar to Example 42, diethyl 2-(2-fluoro-4-biphenylyl)-2-methylmalonate VI under slightly varying conditions is obtained in yields varying from 53–61%.

EXAMPLE 43

Diethyl 2-(2-fluoro-4-biphenylyl)-2-methylmalonate VI with the Alkyl Nitrate Procedure

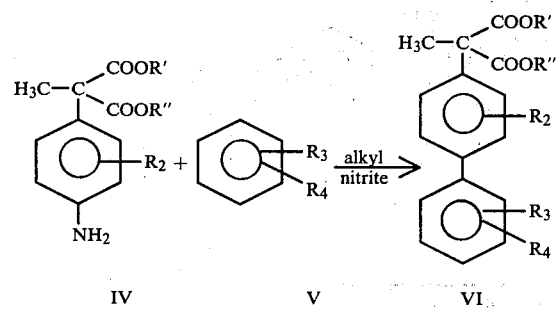

In a one-liter round-bottom flask is placed 250 ml of benzene V. A solution of ~9.1 g (from 31.44 mmol) of diethyl 2-(3-fluoro-4-aminophenyl)-2-methylmalonate IV in 110 ml benzene is placed in one funnel and a solution of 10.1 g (86.5 mmol, 2.75 equiv.) isoamyl nitrite in 50 ml benzene is placed in the other. With vigorous stirring at ~58° C., 0.35 g (3.0 mmol) of isoamyl nitrite is added to the reaction flask. The solutions of amine and nitrite are added simultaneously over 7 hours. When addition is complete, stirring is continued for 4 hours at ~59° C. and the mixture is then allowed to stand for 12 hours. The solvent is removed in vacuo and the resulting dark brown oil (12.0 g) is transferred to a 250 ml separatory funnel. Ice cold 85% (v/v) aqueous sulfuric acid (16 ml) is added and the mixture is extracted with 4×120 ml hexane. The combined hexane extracts are washed with 4×100 ml of 1 M aqueous sodium carbonate, 50 ml of saturated aqueous sodium sulfate solution, and are dried over anhydrous sodium sulfate. Concentration in vacuo gives 6.32 g of 2-(2-fluoro-4-biphenylyl)-2-methylmalonate VI as a yellow oil (58.0% based on 2,4-difluoronitrobenzene II).

In a manner similar to Example 43, diethyl 2-(2-fluoro-4-biphenylyl)-2-methylmalonate is obtained under varying conditions in a yield of 52–72%.

EXAMPLE 44

2-(2-fluoro-4-biphenyl)propionic acid (flurbiprofen)Ib.

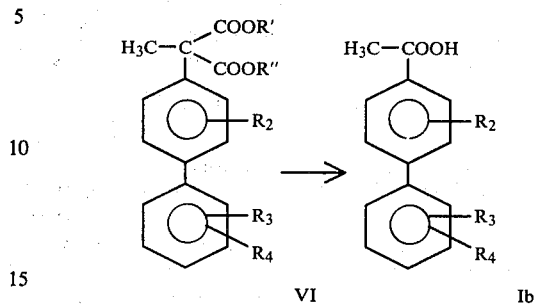

Method A

To a stirred solution of 7.58 g (22.0 mmol) of diethyl 2-(2-fluoro-4-biphenyl)-2-methylmalonate VI in 50 ml of absolute ethanol, maintained under nitrogen gas at ~15° C. (ice bath) is added 8.72 g (109.0 mmol, 5.0 mol-equiv.) of 50% aqueous sodium hydroxide. The temperature is maintained at <25° C. for 6 hours. The resulting suspension is diluted with 150 ml water and the pH is adjusted to ~8.0 with dilute hydrochloric acid. The solution is transferred to a separatory funnel and is extracted with 3×60 ml of methylene chloride. The aqueous layer is acidified to pH <1 with concentrated hydrochloric acid and is then extracted with 200 ml of ethyl acetate in three portions. The combined extracts are dried over anhydrous sodium sulfate and concentrated in vacuo to give 5.9 g 2-(2-fluoro-4-biphenyl)-2-methyl malonic acid. This material is dissolved in 15 ml of glacial acetic acid and the solution is heated to reflux for ~17 hours. Water (15 ml) is added and the solution is allowed to cool slowly with stirring and seeding. After 1 hour stirring at room temperature, the mixture is cooled with stirring to 0°–5° C., then let stand for ~15 hours. The product is isolated and washed with a few ml of cold 50% aqueous acetic acid then dried to give 4.67 g flurbiprofen Ib of melting point 113°–115° C.

Method B

In a 200 ml round-bottom flask is placed 15.03 g (~43.7 mmol) of ethyl 2-(2-fluoro-4-biphenylyl)-2-methylmalonate, 62 ml of glacial acetic acid, and 22 ml of 6 N aqueous hydrochloric acid. The mixture is refluxed under nitrogen for 24 hours. On cooling to room temperature, the solution is diluted with 250 ml of water and the mixture is extracted with 4×50 ml of methylene chloride. The combined extracts are washed with 2×100 ml of water and then with 8×40 ml (0.2 N) of aqueous potassium hydroxide solution. Extracts 1-4 are combined, acidified to pH <1 with concentrated hydrochloric acid, and the resulting solution is extracted with 3×50 ml of methylene chloride. The organic extracts are dried over sodium sulfate and concentrated in vacuo to give 7.13 g (38.8% overall) crude flurbiprofen. Extract 5 is backwashed with 3×5 ml methylene chloride, acidified with concentrated hydrochloric acid, and the resulting mixture is extracted with 3×20 ml methylene chloride to give 1.84 g (10.0%) crude flurbiprofen. Fractions 6-8 are combined and the pH is adjusted to ~9.0. After washing with 3×30 ml methylene chloride, the aqueous is acidified with concentrated hydrochloric acid and is then extracted with 3×50 ml of methylene chloride. Drying and concentration of the extracts gives 0.53 g (4.0%) crude flurbiprofen Ib.

The combined crude flurbiprofen Ib (9.5 g) is crystallized from 59 ml of 50% aqueous acetic acid as previously described to give 8.80 g of flurbiprofen Ib (82.6% conversion from malonate VI; 47.9% overall from 2,4-difluoronitrobenzene II).

Method C

In a 200 ml round bottom flask is placed 10.0 g (~29.1 mmol) of diethyl 2-(2-fluoro-4-biphenylyl)-methylmalonate VI, 9.4 g (167.9 mmol, 6 equiv.) of solid potassium hydroxide, 33 ml of absolute ethanol, and 60 ml water. The resulting two-phase mixture is stirred under reflux for 17 hours. Most of the ethanol is removed in vacuo and the residue is diluted with 100 ml water. The pH is adjusted to ~8 with hydrochloric acid. The aqueous solution is extracted with 5×100 ml methylene chloride. The aqueous layer is acidified with 6 N hydrochloric acid to a pH ~1 and is then extracted with 50 ml of methylene chloride and 3×50 ml of ethyl acetate. The combined organic extracts are washed with dilute aqueous sulfate solution and dried over anhydrous sodium sulfate. Concentration in vacuo gives 6.38 g of tan solids. This material is dissolved in 12 ml of glacial acetic acid and the solution is heated to reflux for 17 hours at which time activated charcoal (Darco G-70) (600 mg) is added. After an additional 3 hours the solution is filtered and the filtrate is diluted with water to give ca. 50% aqueous acetic acid solution. On seeding at ~80° C. and further cooling, the product crystallizes to give an isolation 5.63 g (45.3%) overall yield) of flurbiprofen Ib.

EXAMPLE 45

Ethyl 2-(2-fluoro-4-biphenylyl)propionate

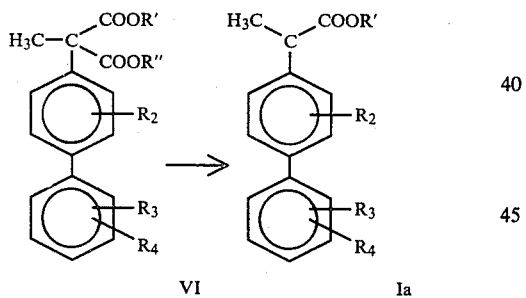

A mixture of 100 millimoles diethyl 2-(2-fluoro-4-biphenylyl)-methylmalonate VI, 110 millimoles sodium chloride, 200 millimoles water and 50 milliliters dimethyl sulfoxide is heated under nitrogen at about 130° to 180° C. for about 6 hours. On cooling the mixture is diluted with 100 milliliters water and 100 milliliters ethyl acetate. The layers are separated and the organic layer is washed two times with 25 milliliters of water. After drying over disodium sulfate the organic layer is concentrated in vacuo to give the desired ethyl 2-(2-fluoro-4-biphenylyl)propionate.

It is understood that novel compounds IIIa and IVa include mono and diacids of esters thereof. The esters can be converted by known methods such as hydrolysis and therefore the acids are novel compounds also within this invention.

We claim:

1. A process for the preparation of a compound selected from the group consisting of

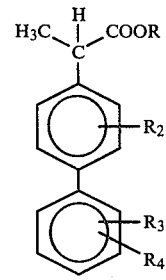

wherein $R_2$ is selected from the group consisting of hydrogen, halogen, alkoxy of from 1 to 6 carbon atoms, inclusive, alkyl of from 1 to 6 carbons, inclusive, cycloalkyl of from 4 to 7 carbons, inclusive, phenyl, and cyano; $R_3$ and $R_4$ are the same or different and are selected from the group consisting of hydrogen, hydroxyl, halogen, nitro, alkyl of from 1 to 6 carbons, inclusive, alkoxy of from 1 to 6 carbons, inclusive, phenyl, cyano, and cycloalkyl of from 4 to 7 carbons, inclusive, and R is selected from the group consisting of hydrogen and alkyl of from 1 to 6 carbons, inclusive, which comprises (1) reacting a compound selected from the group consisting of

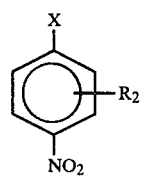

with a compound having the formula

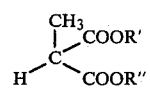

in the presence of a base comprising sodium hydride, sodium hydroxide, potassium hydroxide, or potassium carbonate to prepare a compound selected from the group consisting of

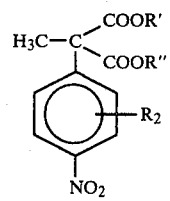

wherein X is halogen, R' and R" are the same or different and are alkyl of from 1 to 6 carbons, inclusive, or R' and R" taken together to form a cyclic diester comprising 2,2-dialkyl-1,3-dioxane-4,6-dione and $R_2$ is as defined above;

(2) reducing the nitro group of compound III from step 1 to produce a compound selected from the group consisting of

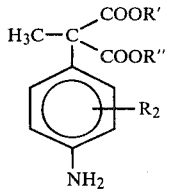

wherein R', R" and R₂ are all defined as above;
(3) coupling the compound IV of step 2 with a compound having the formula

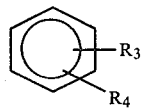

to produce a compound selected from the group consisting of

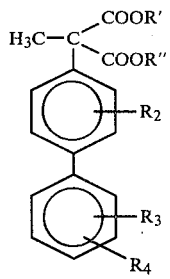

wherein R', R", R₂, R₃ and R₄ are defined as above; and
(4) treating the product VI of step 3 wherein treating the product VI is decarboxylation, decarboxylation and hydrolysis or hydrolysis and decarboxylation to obtain the compound selected from the group consisting of I above.

2. A process according to claim 1 wherein the base in step 1 is selected from the group consisting of alkali metal hydroxide and potassium carbonate.

3. A process according to claim 2 wherein the base is sodium hydroxide.

4. A process according to claim 1 wherein said coupling reaction is conducted in the presence of copper.

5. A process according to claim 1 wherein the coupling consists essentially of reaction the compound IV with aqueous metal nitrile in the presence of the compound V and an acid.

6. A process according to claim 5 wherein the compound IV and an acid are each simultaneously added to a mixture of aqueous sodium nitrile in an excess of the compound V such that molar amounts of sodium nitrite to compound IV is in the range from 1 to 4 times and molar amounts of acid to compound IV is in the range from 1 to 4 times.

7. A process according to claim 6 wherein the acid is sulfuric or acetic acid.

8. A process according to claim 6 wherein the acid is fluoboric acid.

9. A process according to claim 4 wherein the coupling consists essentially of reacting the compound IV with nonaqueous metal nitrite in the presence of the compound V and an organic acid comprising benzoic, chloroacetic, dichloroacetic, trichloacetic, methanesulfonic, or acetic acid.

10. A process according to claim 9 wherein the compound IV and an acid are each simultaneously added to a mixture of finely divided potassium nitrite in an excess of the compound V such that molar amounts of potassium nitrite to compound IV is in the range from 1 to 4 times and molar amounts of acid to compound IV is in the range from 1 to 4 times.

11. A process according to claim 10 wherein the acid is acetic acid.

12. A process according to claim 1 or 4 wherein the coupling comprises reaction of the compound IV with an alkyl nitrite in which alkyl is from 3 to 8 carbons, inclusive, in the presence of an excess of compound V by adding the compound IV and alkyl nitrite simultaneously to the compound.

13. A process according to claim 1 wherein treating comprises decarboxylation of the compound VI so that R in the compound I obtained is alkyl of from 1 to 6 carbons.

14. A process according to claim 13 wherein treating is hydrolyzing and decarboxylating compound VI wherein R₂ is fluorine in a position ortho to the biaryl linkage and R, R₃ and R₄ are hydrogen so that the specific embodiment of compound I obtained is 2-(2-fluoro-4-biphenylyl)propionic acid.

15. A process according to claim 1 wherein treating is decarboxylating compound VI wherein R₂ is fluorine in a position ortho to the biaryl linkage; R is alkyl of from 1 to 6 carbons, inclusive, and R₃ and R₄ are hydrogen so that the specific embodiment of compound I obtained is the alkylester of 2-(2-fluoro-4-biphenyl)propionic acid.

16. A process according to claim 15 wherein R₂ is fluorine in a position ortho to the biaryl linkage, R₃ and R₄ are hydrogen and R is ethyl so that the specific embodiment of compound I obtained is ethyl 2-(2-fluoro-4-biphenylyl)propionate.

17. A process for the preparation of a compound selected from the group consisting of

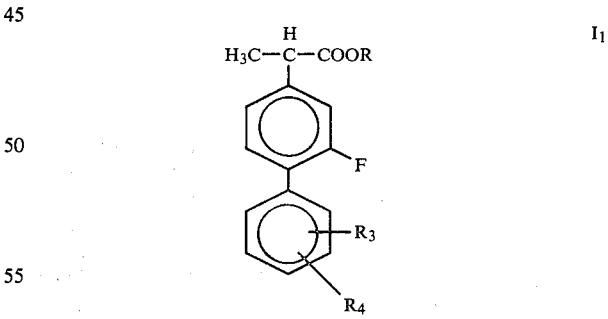

wherein R₃ and R₄ are the same or different and are selected from the group consisting of hydroxyl, hydrogen, halogen, nitro, alkyl of from 1 to 6 carbons, inclusive, alkoxy of from 1 to 6 carbons, inclusive, phenyl, cyano, and cycloalkyl of from 4 to 7 carbons, inclusive, and R is selected from the group consisting of hydrogen and alkyl of from 1 to 6 carbons, inclusive, which comprises (1) reacting a compound selected from the group consisting of

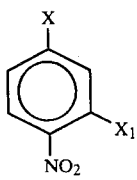

II with a compound having the formula

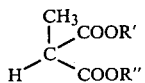

in the presence of a base comprising sodium hydride, sodium hydroxide, potassium hydroxide, or potassium carbonate to prepare a compound selected from the group consisting of

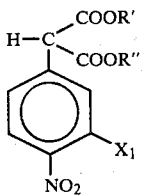

III wherein X and $X_1$ may be the same or different and are halogen, R' and R" are the same or different and are alkyl of from 1 to 6 carbons, inclusive, or R' and R" taken together to form a cyclic diester comprising 2,2-dialkyl-1,3-dioxane-4,6-dione, and with the proviso that $X_1$ is a halogen atom of no greater reactivity than X;

(2) reacting compound III with alkali fluoride to obtain a compound having the formula

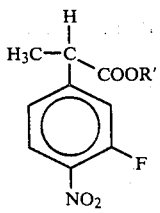

III'a (3) reducing the nitro group of compound III'a from step (2) to produce a compound selected from the group consisting of

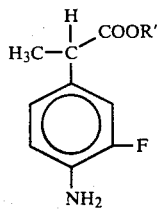

IV'a wherein R' is defined as above;

(4) coupling the compound IV'a of step 3 with a compound having the formula

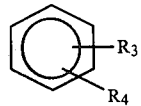

V to produce a compound selected from the group consisting of

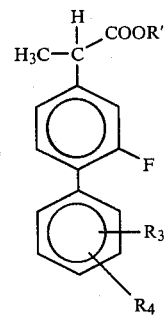

I' wherein R', $R_3$ and $R_4$ are defined as above.

18. A process according to claim 17 wherein the base in step 1 is selected from the group consisting of alkali metal hydroxide and potassium carbonate.

19. A process according to claim 18 wherein the base is sodium hydroxide.

20. A process according to claim 17 wherein said coupling reaction is conducted in the presence of copper.

21. A process according to claim 17 wherein the coupling consists essentially of reacting the compound IV'a with aqueous metal nitrite in the presence of the compound V and an acid.

22. A process according to claim 21 wherein the compound IV'a and an acid are each simultaneously added to a mixture of aqueous sodium nitrite in an excess of the compound V such that molar amounts of sodium nitrite to compound IV'a is in the range from 1 to 4 times and molar amounts of acid to compound IV'a is from 1 to 4 times.

23. A process according to claim 22 wherein the acid is sulfuric or acetic acid.

24. A process according to claim 22 wherein the acid is fluoboric acid.

25. A process according to claim 20 wherein the coupling consists essentially of reacting the compound IV'a with nonaqueous metal nitrite in the presence of the compound V and an organic acid comprising benzoic, chloroacetic, dichloroacetic, trichloroacetic, methanesulfonic, or acetic acid.

26. A process according to claim 25 wherein the compound IV'a and an acid are each simultaneously added to a mixture of finely divided potassium nitrite in an excess of the compound V such that molar amounts of potassium nitrite to compound IV'a is in the range from 1 to 4 times and molar amounts of acid to compound IV'a is in the range from 1 to 4 times.

27. A process according to claim 26 wherein the acid is acetic acid.

28. A process according to claim 17 or 20 wherein the coupling comprises reaction of the compound IV'a with an alkyl nitrite in which alkyl is from 3 to 8 carbons, inclusive, in the presence of an excess of compound V by adding the compound IV'a and alkyl nitrite simultaneously to the compound.

29. A process according to claim 25 wherein compound I' is hydrolyzed to obtain the specific embodiment of compound I having R, $R_3$ and $R_4$ as hydrogen so that the compound I obtained is 2-(2-fluoro-4-biphenylyl)propionic acid.

30. A process according to claim 26 wherein $R_2$ is fluorine in a position ortho to the biaryl linkage, $R_3$ and $R_4$ are hydrogen and R' is ethyl so that the specific embodiment of compound I obtained is ethyl 2-(2-fluoro-4-biphenylyl)propionate.

31. A process for the preparation of a compound selected from the group consisting of

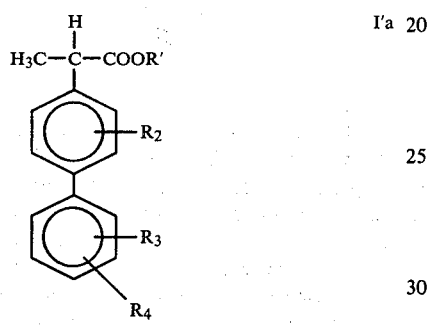

I'a wherein $R_2$ is selected from the group consisting of hydrogen, halogen, alkoxy of from 1 to 6 carbons, inclusive, alkyl of from 1 to 6 carbons, inclusive, cycloalkyl of from 4 to 7 carbons, inclusive, phenyl, and cyano $R_3$ and $R_4$ are the same or different and are selected from the group consisting of hydrogen, hydroxyl, halogen, nitro, alkyl of from 1 to 6 carbons, inclusive, alkoxy of from 1 to 6 carbons, inclusive, phenyl, cyano, and cycloalkyl of from 4 to 7 carbons, inclusive, and R' is alkyl of from 1 to 6 carbons, inclusive, which comprises (1) reacting a compound selected from the group consisting of

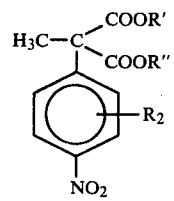

II with a compound having the formula

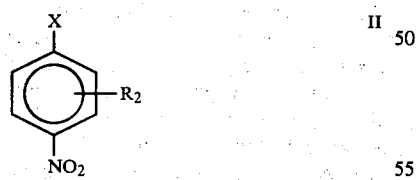

in the presence of a base comprising sodium hydride, sodium hydroxide, potassium hydroxide, or potassium carbonate to prepare a compound selected from the group consisting of

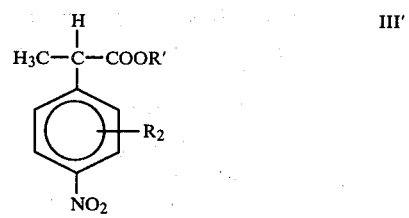

III wherein X is halogen, R' and R" are the same or different and are alkyl of from 1 to 6 carbons, inclusive, or together form a cyclic diester comprising 2,2-dialkyl-1,3-dioxane-4,6-dione, and $R_2$ is as defined above;

(2) treating the compound III of step 1 to produce a compound selected from the group consisting of

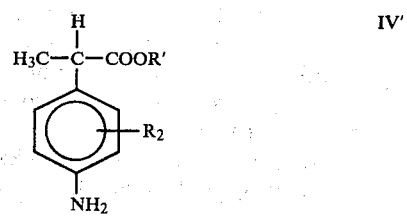

III' wherein R' and $R_2$ are defined as above;

(3) reducing the nitro group of compound III' from step 2 to produce a compound selected from the group consisting of

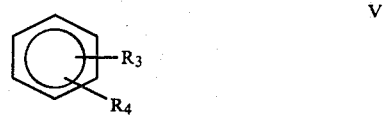

IV' wherein R' and $R_2$ are all defined as above; and (4) coupling the compound IV' of step 3 with a compound having the formula

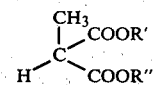

V to produce the compound I'a above.

32. A process according to claim 31 wherein the base in step 1 is selected from the group consisting of alkali metal hydroxide and potassium carbonate.

33. A process according to claim 32 wherein the base is sodium hydroxide.

34. A process according to claim 31 wherein said coupling reaction is conducted in the presence of copper.

35. A process according to claim 31 wherein the coupling consists essentially of reacting the compound IV' with aqueous metal nitrite in the presence of the compound V and an acid.

36. A process according to claim 35 wherein the compound IV' and an acid are each simultaneously added to a mixture of aqueous sodium nitrite in an excess of the compound V such that molar amounts of sodium nitrite to compound IV' is in the range from 1 to 4 times and molar amounts of acid to compound IV' is from 1 to 4 times.

37. A process according to claim 36 wherein the acid is sulfuric or acetic acid.

38. A process according to claim 36 wherein the acid is fluoboric acid.

39. A process according to claim 34 wherein the coupling consists essentially of reacting the compound IV' with nonaqueous metal nitrite in the presence of the compound V and an organic acid comprising benzoic, chloroacetic, dichloroacetic, trichloroacetic, methanesulfonic, or acetic acid.

40. A process according to claim 39 wherein the compound IV' and an acid are each simultaneously added to a mixture of finely divided potassium nitrite in an excess of the compound V such that molar amounts of potassium nitrite to compound IV' is in the range from 1 to 4 times and molar amounts of acid to compound IV' is in the range from 1 to 4 times.

41. A process according to claim 40 wherein the acid is acetic acid.

42. A process according to claim 31 or 34 wherein the coupling comprises reaction of the compound IV' with an alkyl nitrite in which alkyl is from 3 to 8 carbons, inclusive, in the presence of an excess of compound V by adding the compound IV' and alkyl nitrite simultaneously to the compound.

43. A process according to claim 42 wherein $R_2$ is fluorine in a position ortho to the biaryl linkage, $R_3$ and $R_4$ are hydrogen and R' is ethyl so that the specific embodiment of compound I obtained is ethyl-2-(2-fluoro-4-biphenylyl)propionate.

44. A process for the preparation of a compound selected from the group consisting of

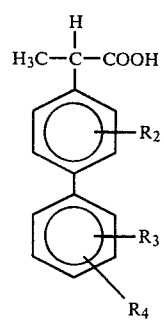

wherein $R_2$ is selected from the group consisting of hydrogen, halogen, alkoxy of from 1 to 6 carbons, inclusive, alkyl of from 1 to 6 carbons, inclusive, cycloalkyl of from 4 to 7 carbons, inclusive, phenyl, and cyano; $R_3$ and $R_4$ are the same or different and are selected from the group consisting of hydrogen, hydroxyl, halogen, nitro, alkyl of from 1 to 6 carbons, inclusive, alkoxy of from 1 to 6 carbons, inclusive, phenyl, cyano, and cycloalkyl of from 4 to 7 carbons, inclusive, and R is selected from the group consisting of hydrogen and alkyl of from 1 to 6 carbons, inclusive, which comprises (1) reacting a compound selected from the group consisting of

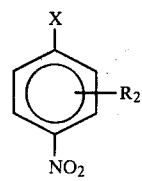

with a compound having the formula

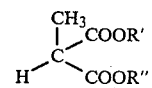

in the presence of a base comprising sodium hydride, sodium hydroxide, potassium hydroxide, or potassium carbonate to prepare a compound selected from the group consisting of

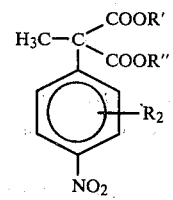

wherein X is halogen, R' and R" are the same or different and are alkyl of from 1 to 6 carbons, inclusive, or together form a cyclic diester comprising 2,2-dialkyl-1,3-dioxane-4,6-dione, and $R_2$ is as defined above;

(2) treating the compound III of step 1 to produce a compound selected from the group consisting of

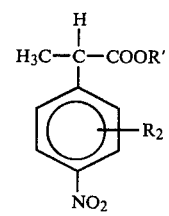

wherein R' and $R_2$ are defined as above;

(3) reducing the nitro group of compound III from step 2 to produce a compound selected from the group consisting of

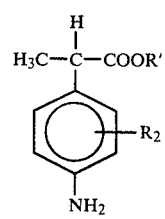

wherein R' and $R_2$ are all defined as above;

(4) coupling the compound IV' of step 3 with a compound having the formula

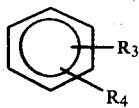

to produce a compound selected from the group consisting of

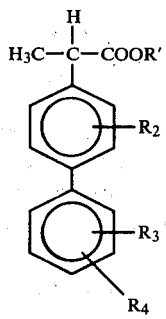

wherein R′, $R_2$, $R_3$ and $R_4$ are defined as above; and (5) hydrolyzing the compound Ia to make the compound Ib.

45. A process according to claim 44 wherein the base in step 1 is selected from the group consisting of alkali metal hydroxide and potassium carbonate.

46. A process according to claim 45 wherein the base is sodium hydroxide.

47. A process according to claim 44 wherein said coupling reaction is conducted in the presence of copper.

48. A process according to claim 44 wherein the coupling consists essentially of reacting the compound IV′ with aqueous metal nitrite in the presence of the compound V and an acid.

49. A process according to claim 48 wherein the compound IV and an acid are each simultaneously added to a mixture of aqueous sodium nitrite in an excess of the compound V such that molar amounts of sodium nitrite to compound IV′ is in the range from 1 to 4 times and molar amounts of acid to compound IV′ is from 1 to 4 times.

50. A process according to claim 48 wherein the acid is sulfuric or acetic acid.

51. A process according to claim 49 wherein the acid is fluoboric acid.

52. A process according to claim 47 wherein the coupling consists essentially of reacting the compound IV′ with nonaqueous metal nitrite in the presence of the compound V and an organic acid comprising benzoic, chloroacetic, dichloroacetic, trichloroacetic, methanesulfonic, or acetic acid.

53. A process according to claim 52 wherein the compound IV′ and an acid are each simultaneously added to a mixture of finely divided potassium nitrite in an excess of the compound V such that molar amounts of potassium nitrite to compound IV′ is in the range from 1 to 4 times and molar amounts of acid to compound IV′ is in the range from 1 to 4 times.

54. A process according to claim 53 wherein the acid is acetic acid.

55. A process according to claim 44 or 47 wherein the coupling comprises reaction of the compound IV′ with an alkyl nitrite in which alkyl is from 3 to 8 carbon atoms, inclusive, in the presence of an excess of compound V by adding the compound IV′ and alkyl nitrite simultaneously to the compound.

56. A process according to claim 44 wherein $R_2$ is fluorine in a position ortho to the biaryl linkage and $R_3$ and $R_4$ are hydrogen so that the specific embodiment of compound Ib obtained is 2-(2-fluoro-4-biphenylyl)propionic acid.

* * * * *

UNITED STATES PATENT OFFICE
CERTIFICATE OF CORRECTION

Patent No. 4,324,904        Dated 13 April 1982

Inventor(s) Thomas A. Hylton and Jerry A. Walker

It is certified that error appears in the above-identified patent and that said Letters Patent are hereby corrected as shown below:

Column 1, line 55, "discloses" should read -- disclose --.
Column 10, line 23, "potassum" should read -- potassium --.
Column 11, line 22, "alkai" should read -- alkali --.
Column 13, line 6, "cmbined" should read -- combined --.
Column 14, line 2, "stop" should read -- step --.
Column 16, line 46, "24" should read -- 25 --.
Column 18, line 24, "Nitrate" should read -- Nitrite --.
Column 18, line 61, "nitrate" should read -- nitrite --.
Column 19, line 25, "Nitrate" should read -- Nitrite --.
Column 20, line 6, "$H_3C-COOH$" should read -- $H_3C-\underset{|}{\overset{|}{C}}-COOH$ --.

Column 20, line 20, "biphenyl)" should read -- biphenylyl --.
Column 20, line 34, "biphenyl)" should read -- biphenylyl --.
Column 23, claim 5, line 50, "reaction" should read -- reacting --.
Column 23, claim 6, line 56, "nitrile" should read -- nitrite --.

Signed and Sealed this

Eighth Day of October 1985

[SEAL]

Attest:

DONALD J. QUIGG

Attesting Officer      *Commissioner of Patents and Trademarks—Designate*